(12) United States Patent
Foerster-Klein et al.

(10) Patent No.: US 6,350,234 B1
(45) Date of Patent: Feb. 26, 2002

(54) ENDOSCOPE

(75) Inventors: Thomas Foerster-Klein, Moelln; Jens Juergens, Bargteheide; Holger Frische, Buchholz, all of (DE)

(73) Assignee: Olympus Winter & IBE GmbH, Hamburg (DE)

( * ) Notice: Subject to any disclaimer, the term of this patent is extended or adjusted under 35 U.S.C. 154(b) by 0 days.

(21) Appl. No.: 09/307,127

(22) Filed: May 7, 1999

(30) Foreign Application Priority Data

May 16, 1998 (DE) .......................................... 198 22 167

(51) Int. Cl.7 ................................................. A61B 1/06
(52) U.S. Cl. ....................... 600/161; 600/129; 600/133; 385/117
(58) Field of Search ................................ 600/161, 121, 600/125, 133, 138, 182; 385/117, 118

(56) References Cited

U.S. PATENT DOCUMENTS 4,354,734 A    10/1982  Nakahashi et al. ...... 350/96.26
5,199,417 A  *  4/1993  Muller et al. ................ 600/138
5,347,990 A  *  9/1994  Ebling et al. ................ 600/182
5,711,756 A     1/1998  Chikama ..................... 600/112

FOREIGN PATENT DOCUMENTS

DE    26 37 133      2/1978
DE    195 42 955     5/1997

* cited by examiner

*Primary Examiner*—John Mulcahy
(74) *Attorney, Agent, or Firm*—Rankin, Hill, Porter & Clark LLP

(57) ABSTRACT

An endoscope has a distal objective and proximal devices for image viewing including a fiber optical image guide, which extends within the endoscope between the objective and the devices for viewing the image and one of whose end regions is fixedly mounted on the endoscope and the other end region of which is axially movably mounted, and the image guide is secured in its proximal end region and the remaining distal end region of the image guide is freely movable, the objective also being movably received relative to the endoscope and the distal end of the image guide and the objective being connected together for common axial movement.

8 Claims, 1 Drawing Sheet

ENDOSCOPE

FIELD OF THE INVENTION

This invention relates to an endoscope

BACKGROUND OF THE INVENTION

Endoscopes (also referred to as endoscopic optical systems) of the type to which the invention relates generally have a proximal main body, distally connected to which there is a tubular shaft region. In such devices, e.g. ureterscopes, the shaft region is of rigid construction and has a relatively small diameter in comparison to its length. Fibrous light guides can be positioned in the tubular shaft region, also termed cover tube or optical tube, which extend from a proximal entry point in the vicinity of the main body to the distal end of the optical tube, and serve to illuminate the field to be observed. Furthermore, the optical tube accommodates the actual devices for transmitting the image, optionally in a further tube (system tube).

The image transmission occurs between a lens provided in the distal end region of the system tube and a proximal device for image viewing, e.g., an eyepiece or a video camera, etc.

Particularly in endoscopes with a small diameter, a so-called fiber optic image guide is used for transmission. The image guide extends between the distal lens and the proximal image viewing devices. Such a fiber optic image guide comprises a plurality of longitudinally extending fibers of transparent material, particularly of materials based on glass, e.g., quartz glass.

A substantial problem with conventional endoscopes in this connection is that the used image guides of, e.g., quartz glass have different expansion characteristics from the surrounding regions of the endoscope, e.g., the system tube, which comprises metal.

In particular, a rigid endoscope of small diameter, e.g., a ureterscope, must be able to withstand bending of its shaft region during use. The image guide is generally not centrally disposed so that bending of the endoscope results in stretching or buckling which can be accommodated by the metallic system tube without great problems but can be accommodated only to a limited extent by a fixed "glass fiber" image guide positioned therein. Similar problems occur when heat sterilizing endoscopes with fiber optic image guides. The image guide and endoscope expand to different extents and at different speeds from each other and stresses can thus occur, particularly if both ends of the image guide are fixed.

There are various possibilities for dealing with the above problems. In this connection, e.g., WO 9605764 discloses an endoscope of the type referred to above in which the image guide is fastened in the system tube only at its distal end. The proximal end, on the other hand, is movably received in the main body. A disadvantage with this known construction is that, particularly having regard to the very short focal lengths of the optical components which are used, a correction must be effected each time the proximal end of the image guide moves, which necessitates a relatively large construction expense.

SUMMARY OF THE INVENTION

It is thus an object of the invention, starting from the prior art, to provide an endoscope in which the occurrence of stresses between the image guide and endoscope can be prevented at low constructional expense.

In the endoscope in accordance with the invention it is provided that the image guide is fixedly secured in the endoscope substantially only at its proximal end region while the remaining image guide region to its distal end is mounted to be freely movable in the axial direction.

In conventional devices, which have a main body and a shaft attached thereto, the fastening of the image guide is effected, e.g., in the region of the main body while its region situated within the shaft is not fixed. Potential thermal influences or bending, which result in differential elongation of the image guide and the surrounding endoscope, can thus be compensated for without difficulty, the distal end of the image guide moving in the axial direction with respect to the endoscope. In order to make constant optical imaging quality possible, the invention further provides that the objective is also mounted movably with respect to the endoscope and is so connected to the distal end of the image guide that common movement occurs with a constant spacing.

The term "objective" means any and all optical devices which make imaging of the field of view at the distal end of the image guide possible. It can be a lens or lens system, wherein the connection between the image guide and objective can be effected, e.g., by adhesive. Other types of connection are, however, also possible.

The invention is preferably implemented in a rigid endoscope of small diameter, i.e., an endoscope which has a main body, from which a rigid, relatively long shaft region of small diameter extends. Such an endoscope can be bent within limits during use, whereby the relative movement described above between the image guide and endoscope occurs which is compensated for in a particularly simple manner in devices in accordance with the invention.

The proximal end of the image guide is generally fixedly mounted in the main body of the endoscope. For this purpose, an appropriate fastening device, for instance, can be provided in the main body which holds the proximal end of the image guide at a constant distance from the image viewing devices. The remaining region of the image guide is held freely axially movable up to its distal end, the distally provided objective being axially movably mounted with respect to the endoscope and connected to the distal end of the image guide.

It would be possible, e.g., for the objective to be a single, e.g., gradient lens which is secured by adhesive to the distal end of the image guide. A further advantageous embodiment of the invention provides that the objective is accommodated in an objective tube which is mounted to be axially movable with respect to the endoscope or the surrounding system tube. The distal end of the image guide is connected by adhesive or the like to the proximal end of the objective tube or to the proximal lens of the objective. This embodiment may be realized in a particularly simple manner, particularly if the objective comprises a number of lenses, and allows simultaneous tolerance-free movement of the light guide and objective.

It can be provided in a further advantageous embodiment that the objective tube or the objective is received in the endoscope secured against rotation. This can be achieved, e.g., by providing an elongated projection on the objective tube which engages in a suitable groove in the system tube.

The advantages of the invention reside substantially in the particularly simple constructional implementation with which an optimum optical imaging quality is always ensured, even under widely varying operational conditions. Due to the fact that the distal objective is axially movably accommodated in the endoscope and is automatically appropriately moved axially in the event of potential, e.g., thermally induced, changes in length of the image guide while maintaining the optical conditions, particularly simple adjustment is possible.

BRIEF DESCRIPTION OF THE DRAWINGS

The invention will be explained in more detail with reference to the accompanying drawings wherein.

DESCRIPTION OF PREFERRED EMBODIMENTS

Figure 1:
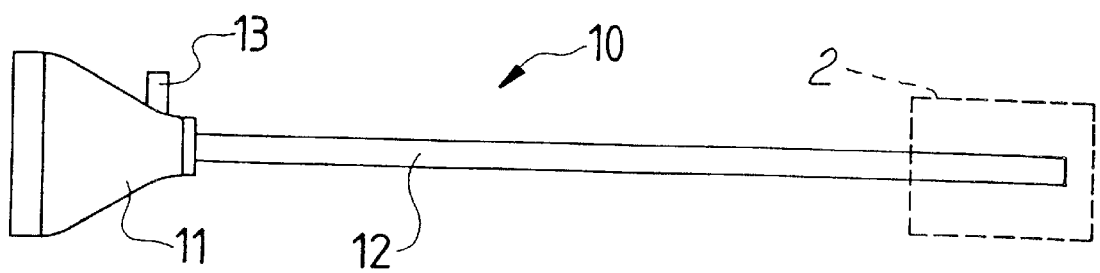
FIG. 1 is a side view of a rigid endoscope in which the invention can preferably be implemented.

A conventional rigid endoscope 10 is shown in FIG. 1 with a main body 11 and an elongated tubular shaft region (optical tube 12) distally connected thereto. Also indicated is a connection 13 by which a light guide, which is not shown in FIG. 1, is inserted into the interior of optical tube 12. An eyepiece or a CCD camera or an interface for appropriate observation devices is generally provided in main body 11. These components are also not shown in detail.

Figure 2:
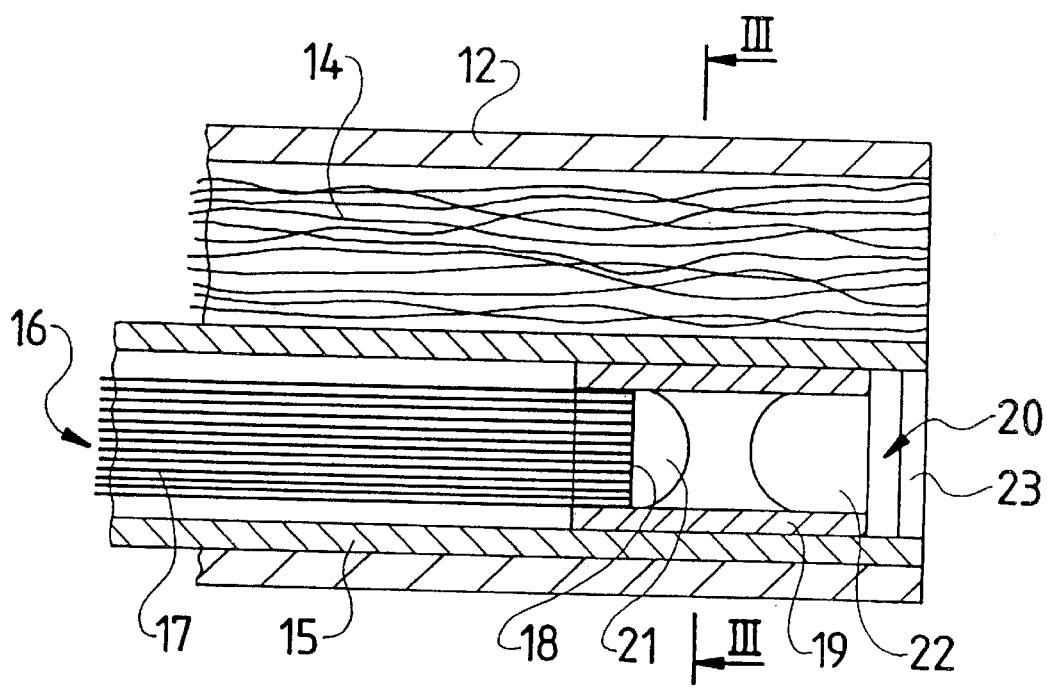
FIG. 2 is a partial longitudinal sectional view, substantially enlarged, of the distal region 2 indicated in FIG. 1.

FIG. 2 is a detailed longitudinal sectional view of distal region 2 of optical tube 12 of FIG. 1. Accommodated within optical tube 12 is a fiber bundle 14, which extends in the axial direction and serves as a light guide to illuminate the field of view. Also provided in optical tube 12 is a so-called system tube 15 in which an image guide 16 is accommodated. As may be seen in FIG. 2 and also in FIG. 3, image guide 16 and the surrounding system tube 15 do not extend centrally but are eccentrically mounted with respect to the cross-section which can lead to the stretching or crushing described above, if the endoscope 10 is bent.

Image guide 16 has axially extending, optically conductive fibers 17 of transparent material, e.g. quartz glass, and extends from the illustrated distal end of optical tube 12 into main body 11 of endoscope 10, in which its proximal end, as described above, is stationarily fixed in position. The remaining, i.e. non-fixed, portion of image guide 16 is freely axially movably mounted, so that differing changes in length of the image guide and surrounding endoscope 10 as a result of their materials can be compensated for without problem by relative axial movement of distal end 18 of image guide 16.

Also provided is an objective tube 19, which is axially movably mounted in system tube 15 and in which an objective 20, comprising two optical lenses 21 and 22, is received. As illustrated, distal end 18 of the light guide is inserted into the proximal end region of optical tube 19 and, e.g., secured there by adhesive to the facing surface of lens 21. System tube 15 is sealed from the exterior against moisture etc. by a window 23.

The illustrated construction permits length compensation of image guide 1 with respect to system tube 15 in a particularly simple manner without subsequent optical adjustment being necessary between image guide 16 and objective 20. If a change in length occurs with an axial movement of distal end 18 of image guide 16, objective 20 automatically then adjusts itself by moving axially in system tube 15.

Figure 3:
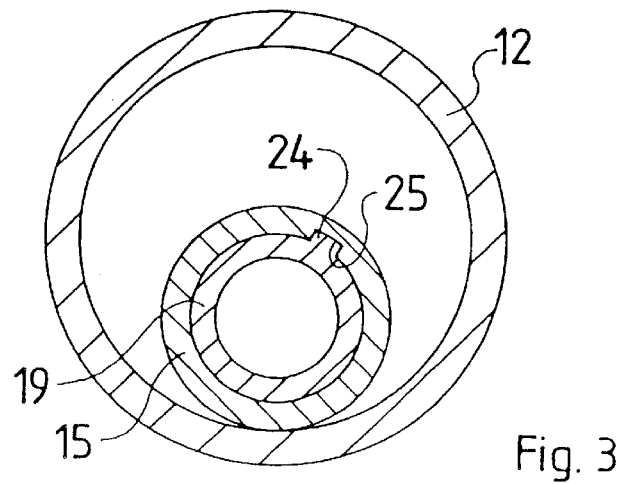
FIG. 3 is a transverse sectional view along line III—III of FIG. 2.

FIG. 3 is a sectional view substantially of the construction described above. One can see optical tube 12, system tube 15 eccentrically disposed within it and optical tube 19 which is axially slidably guided within system tube 15. The details of the optical components, such as the light guide, image guide, lenses, etc. have been omitted for reasons of clarity. In addition to what is shown in FIG. 2, one can, however, see in FIG. 3 that the optical tube has a projection 24 on its external periphery which is slidably received in a groove 25 in system tube 15. Security against rotation of objective 20 is ensured in this manner.

The illustrated construction is only one possibility of implementing the invention. It would also be possible, for instance, to fasten the objective to the image guide without a surrounding objective tube. The invention further relates not only to endoscopes with a "thin" shaft but also to all rigid devices with fiber optical image guides. Finally, it is also not essential that light guides are also disposed in the shaft next to the image guide.

What is claimed is:

1. An endoscope comprising:

a distal objective and proximal devices for image viewing; and a fiber optic image guide extending within said endoscope and generally parallel to an axis of said endoscope between said objective and said devices for image viewing, a proximal end region of said image guide being fixedly attached to said endoscope and a distal end region of said image guide being freely axially movably mounted, said objective being movable relative to said endoscope with said distal end of said image guide, said image guide distal end and said objective being connected together for common axial movement, such that thermal expansion can be compensated by axial movement of the image guide distal end and objective relative to said image guide proximal end.

2. An endoscope according to claim 1, comprising a rigid endoscope (10) having a proximal main body (11), a distal tubular rigid shaft region (12) connected thereto, and a system tube (15) in said rigid shaft region to receive said image guide (16).

3. An endoscope according to claim 2 wherein said objective (20) is received in an optical tube (19) which is axially movably mounted in said system tube.

4. An endoscope according to claim 3, wherein said optical tube (19) or said objective is mounted in said system tube (15) and secured against rotation.

5. An endoscope according to claim 1, further comprising a system tube, wherein said image guide and said objective are received within said system tube and said distal end of said image guide and said objective are movable relative to said system tube.

6. The endoscope according to claim 5, comprising a rigid endoscope (10) having a proximal main body (11), a distal tubular rigid shaft region (12) connected thereto, and wherein said system tube (15) is disposed in said rigid shaft region to receive said image guide (16).

7. The endoscope according to claim 6, wherein said objective (20) is received in an optical tube (19) which is axially movably mounted in said system tube.

8. The endoscope according to claim 7, wherein at least one of said optical tube (19) and said objective is mounted in said system tube (15) and secured against rotation.

* * * * *